US008386077B2

(12) United States Patent
Birkenbach et al.

(10) Patent No.: US 8,386,077 B2
(45) Date of Patent: Feb. 26, 2013

(54) METHOD FOR ASSESSING THE POSITIONING ACCURACY OF A MEDICAL ROBOT ARM

(75) Inventors: Rainer Birkenbach, Erding (DE); Richard Wohlgemuth, Bad Tölz (DE)

(73) Assignee: Brainlab AG, Feldkirchen (DE)

( * ) Notice: Subject to any disclaimer, the term of this patent is extended or adjusted under 35 U.S.C. 154(b) by 632 days.

(21) Appl. No.: 12/620,674

(22) Filed: Nov. 18, 2009

(65) Prior Publication Data

US 2010/0131099 A1 May 27, 2010

Related U.S. Application Data

(60) Provisional application No. 61/147,809, filed on Jan. 28, 2009.

(30) Foreign Application Priority Data

Nov. 25, 2008 (EP) .................................... 08169866

(51) Int. Cl.
*G05B 19/04* (2006.01)

(52) U.S. Cl. ........................................... 700/245; 901/1

(58) Field of Classification Search .......... 700/245–249, 700/258–264; 318/568.11, 568.21, 568.12, 318/568.16; 901/1–2, 8–9; 414/1–2
See application file for complete search history.

(56) References Cited

U.S. PATENT DOCUMENTS 7,331,750 B2 * 2/2008 Merz et al. .................... 414/735
7,689,320 B2 * 3/2010 Prisco et al. .................. 700/245
2006/0048364 A1 3/2006 Zhang et al.
2007/0144298 A1 6/2007 Miller

FOREIGN PATENT DOCUMENTS

WO 99/50721 10/1999
WO 02/060653 8/2002

OTHER PUBLICATIONS

Ho et al., "Establishing a force control strategy incorporating active motion contstraint", IEEE Engineering in Medicine and Biology Magazine, May 1995, pp. 292-300.
Muruganandam et al., "Stiffness-based workspace atlas of hexapod machine tool for optimal work piece location", The International Journal of Advanced Manufacturing Technology, Jun. 2008.
Qingsong xu et al., "Stiffness optimization of a 3DOF Parallel Kinematic Machine Using Particle Swarm Optimization", Robotics and Biomimetics, 2006.
Xu et al., "An investigation on mobility and stiffness of a 3-DOF translational available parallel manipulator via screw theory", Robotics and Computer Integrated Manufacturing, Mar. 2008.
European Search Report for corresponding application No. EP 08 169 866.4 dated May 6, 2009.

* cited by examiner

*Primary Examiner* — Dalena Tran

(74) *Attorney, Agent, or Firm* — Renner, Otto, Boisselle & Sklar, LLP

(57) ABSTRACT

A method for assessing the positioning accuracy of a medical robot arm comprising at least one joint, wherein the rigidity of the robot arm in a joint placement is calculated and assessed on the basis of a rigidity model.

22 Claims, 1 Drawing Sheet

1
9
14
8
13
7
6
12
5
4
11
3
10
2

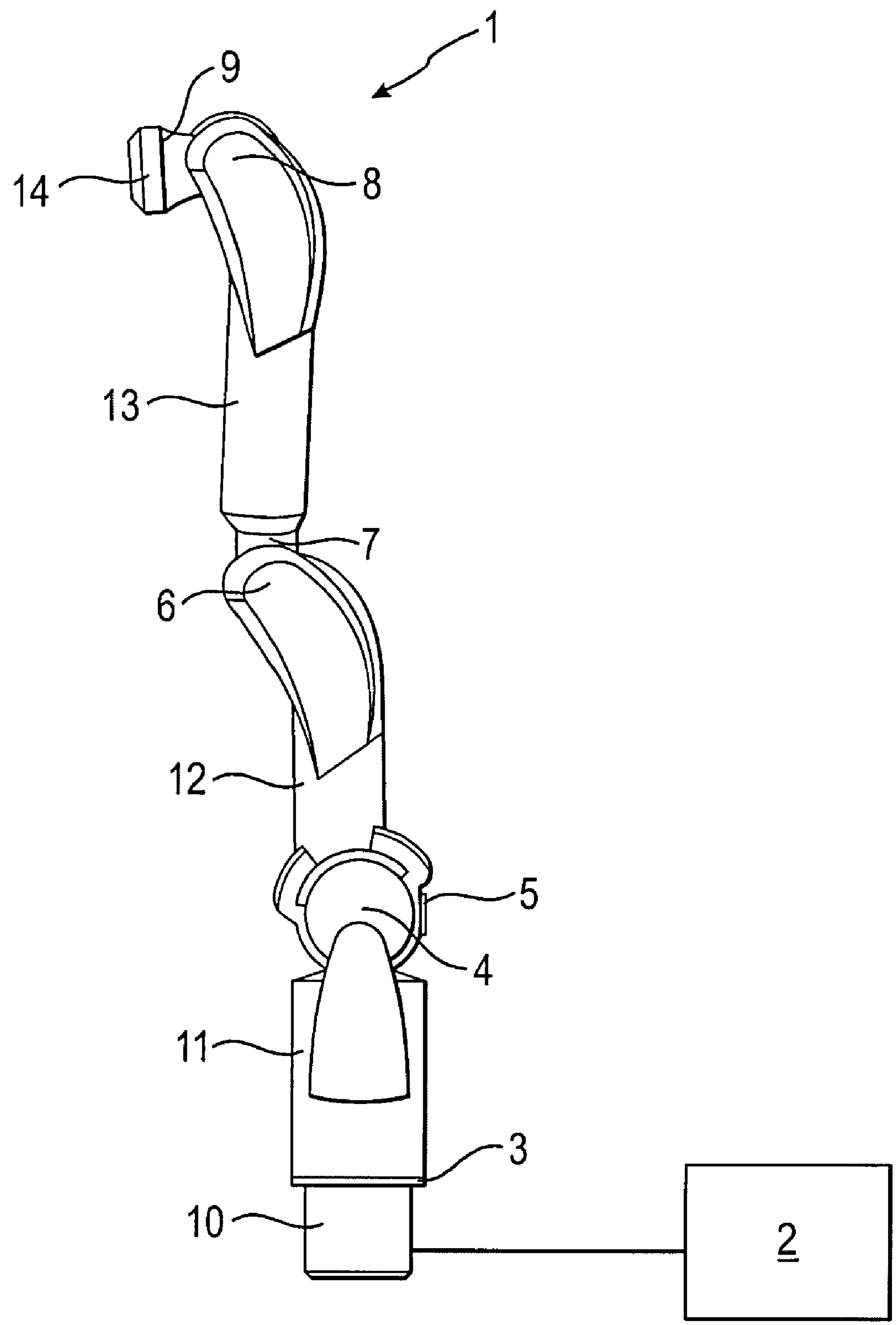
1
9
14
8
13
7
6
12
5
4
11
3
10
2

METHOD FOR ASSESSING THE POSITIONING ACCURACY OF A MEDICAL ROBOT ARM

RELATED APPLICATION DATA

This application claims the priority of U.S. Provisional Application No. 61/147,809, filed on Jan. 28, 2009, which is hereby incorporated in its entirety by reference.

FIELD OF THE INVENTION

The use of robot arms which for example carry a medical instrument is known in medical applications, wherein the robot arm automatically travels a predetermined trajectory or is guided by an operator. It is also possible for the robot arm to travel a predetermined trajectory when touched or acted on with a small force by the user. Document US 2007/144298, for example, describes a robot arm which is restricted in its movement to a predetermined volume. One problem with such robot arms is a possible deviation between the robot arm position and the target position.

SUMMARY OF THE INVENTION

It is the object of the present invention to provide a method using which the positioning accuracy of the medical robot arm can be assessed as precisely as possible.

This object is solved by calculating the rigidity of the robot arm on the basis of a rigidity model and taking this into account when assessing the positioning accuracy.

A robot arm consists of two or more arm sections, wherein each two arm sections are connected to each other via at least one joint. The term "joint" also encompasses—in addition to connecting elements which permit a rotation between two arm sections—connecting elements which enable a translation. An arm section is for example a pipe. The spatial position of the moving end of the robot arm is designated as the position of the robot arm or the robot arm position. The term "joint placement" is understood to mean the entirety of the placements of all the joints of the robot arm. Depending on the embodiment of the robot arm, it is possible to reach the same robot arm position through different joint placements. The placement of a joint is generated by an actuating member such as for example an electric motor, wherein a transmission gear is optionally provided.

The robot arm also comprises a fastening point at which the robot arm is fastened to a structure such as a tripod or other mounting. The working space encompasses a number of positions which the robot arm can reach, wherein this can be a closed or half-open volume, an area or a line.

The rigidity model is a mathematical model of the robot arm, by means of which the overall rigidity of the robot arm can be calculated. The rigidity describes the relationship between a force acting on the robot arm and the deformation of the robot arm. It is dependent among other things on the materials of the robot arm and its geometry. Producing a rigidity model is known to the person skilled in the art and is therefore not explained in more detail.

The assessment is a method step which is subsequent to calculating the rigidity of the robot arm on the basis of the rigidity model, and in which in particular the positioning accuracy is examined according to one or more criteria. The assessment step can for example include at least one of the following steps: comparing the rigidity of the robot arm in a working space to be traveled with a target rigidity; defining the fastening point of the robot arm; outputting notifying information; selecting an optimum joint placement from a number of possible joint placements; or comparing the robot arm position with a measured robot arm position. The assessment step corresponds in particular to an evaluation of the positioning accuracy, in particular on the basis of the calculated rigidity.

Due to the limited rigidity of the robot arm, the actual robot arm position often does not correspond exactly to the calculated or theoretical robot arm position such as is theoretically predetermined by the joint placement. The deviation between the actual robot arm position and the theoretical robot arm position, also referred to as the positional deviation, is a measure of the positioning accuracy and can serve as a basis for subsequent calculation steps.

The deviation is calculated from the rigidity of the robot arm and the forces acting on the robot arm. A high rigidity means a low positional deviation, i.e. a high positioning accuracy, and vice versa. The rigidity is dependent among other things on the joint placement of the robot arm. If a robot arm position can be reached through different joint placements, then the rigidity for this position can be different, i.e. for each joint placement.

In one embodiment of the invention, the rigidity model takes into account the mechanical rigidity. The mechanical rigidity is influenced by one or more of the following factors: the rigidity of the joints; the length of the arm sections; the rigidity of the arm sections; and the rigidity of the transmission gear. The rigidity model alternatively or additionally takes into account the control rigidity of the robot arm. The control rigidity is caused by the—in most cases, electronic—guidance system of the robot arm, which is for example not continuous but cyclic.

Optionally, a force which acts on the robot arm is taken into account when assessing the positioning accuracy. Such a force is for example the force on an instrument at the moving end of the robot arm or the force which an operator exerts on the robot arm. The force acting on the robot arm is preferably ascertained by means of force sensors which are for example arranged in the region of the joints. Alternatively, the force can be a hypothetical force which is assumed to be exerted on the robot arm when the robot arm is used. This is in particular advantageous when planning the working space.

Alternatively or additionally, the inherent weight of the robot arm is taken into account when assessing the positioning accuracy. To this end, each component of the robot arm which is taken into account, i.e. each joint or arm section, is approximated as a punctiform mass and taken into account as a weight force acting in this point.

Optionally, the rigidity and/or positional deviation is not calculated in all spatial directions but rather only in one or two spatial directions. This leads to a reduced computational effort and is in particular expedient when the force does not act from all spatial directions.

In accordance with one embodiment of the invention, a working space which can be traveled by the robot arm is calculated on the basis of the rigidity. The working space is limited by the robot arm positions at which the rigidity reaches a boundary value. A robot arm position at which the rigidity would be below this boundary value cannot therefore be reached by the robot arm. The boundary value is for example defined by an operator and/or is ascertained on the basis of the application scenario for the robot arm. This embodiment represents a method for checking and/or restricting the working space of a robot arm. Alternatively, a rigidity—for example, a minimum, maximum or average rigidity—is calculated for a given working space. Optionally, a check is made as to whether the calculated working space which can be traveled contains the region necessary for an application of the robot arm. This ensures that the rigidity of the robot arm does not fall below a permissible minimum value, i.e. that a maximum permissible deviation in the forces occurring is not exceeded, during the application as a whole.

In another embodiment of the invention, the anchoring point for the robot arm is calculated from the rigidity and the working space to be traveled. The anchoring point is the spatial point at which the robot arm is fixed, via its fastening point, to for example an operating table, wherein the anchoring point is determined such that within the whole of the working space to be traveled, the robot arm maintains and does not fall below a predetermined rigidity. In one embodiment, a number of hypothetical anchoring points are simultaneously assumed, and from them, the anchoring point for which the rigidity exhibits the greatest minimum value or the greatest average value within the working space being checked is selected. This application represents a method for ascertaining the anchoring point of a robot arm.

Optionally, instructions are given to the user as to how the robot arm is to be positioned relative to a structure (an anatomical structure), such that the working space (to be traveled) required for the application lies within the working space which can be reached with the desired rigidity. When calculating the anchoring point, it is in particular possible to incorporate the navigation data which describes the location of the (anatomical) structure. The spatial location of the working space to be traveled also follows from the navigation data.

Optionally, a warning can be output when the robot arm reaches a position at which it falls below a defined boundary value for the rigidity. This is in particular expedient for the application scenario in which the operator pushes the robot arm over a predetermined trajectory with only a small application of force or in which the working space is not restricted. This application represents a method for verifying the working space at the force currently acting on the robot arm. A numerical value of the positional deviation and/or of the rigidity for the current joint placement is optionally also displayed or indicated.

It is possible to output a warning when the force exerted on the robot arm by the user and/or the instrument exceeds a boundary value. These two forces can for example be distinguished by their points of application. At least two force sensors are for example provided for this purpose.

In order to adopt a robot arm position, the joint placement for which the defined criteria regarding the rigidity are fulfilled is preferably selected from a number of possible joint placements. One criterion can for example be a minimum rigidity. If a joint placement is found which reaches or exceeds a defined rigidity, then this joint placement is selected. Alternatively, it is possible to select the joint placement at which the greatest rigidity is achieved. In order to check the rigidity for the criterion or criteria, the rigidity is calculated and assessed for different joint placements on the basis of the rigidity model. This application represents a method for optimizing the joint placement of a robot arm.

If the robot arm is to adopt different positions during an application, it is in most cases undesirable to come across significantly different joint placements for adjacent robot arm positions. In this case, the robot arm would make a discontinuous change to the joint placement in the event of only a small change in position, which would mean a large movement of the robot arm, in particular of the joints or arm sections. In this case, it is desirable to assign joint placements to particular robot arm positions, which do not necessarily achieve the maximum rigidity but do enable a continuous change to the joint placements when the robot arm position is altered. A change is for example continuous when the change in the spatial position of each joint between a first joint placement for a first robot arm position and a second joint placement for a second robot arm position is less than the distance between the two robot arm positions, in particular less than 1 times, 0.9 times, 0.8 times, 0.75 times, 0.5 times, 0.25 times or 0.1 times the distance between the two robot arm positions. This applies to the end state after re-positioning and/or to the transition from one robot arm position to another.

Preferably, a joint placement is selected from which it is possible to reach the whole of the working space using only continuous changes to the joint placement and without falling below a minimum required rigidity. If there are a number of such joint placements, the joint placement which offers the greatest rigidity at the current robot arm position, which deviates the least from the current joint placement or which maximizes a parameter is for example selected. Such a parameter is in particular the minimum, maximum or average rigidity of the robot arm in the working space. For selecting the joint placement, the rigidity is calculated and assessed for different joint placements and robot arm positions on the basis of the rigidity model.

In particular when selecting one joint placement from a number of possible joint placements and calculating the anchoring point of the robot arm, the rigidity is optimally averaged over the working space to be traveled. When averaging, it is possible to assign different weighting factors to positions in different regions of the working space, in order to ensure a greater rigidity in important regions of the working space.

Optionally, the robot arm position calculated on the basis of the rigidity model is compared with a measured robot arm position. To this end, the moving end of the robot arm is preferably provided with a marker device or a reference star. From the difference between the two positions and the forces acting on the robot arm, it is possible to update the rigidity model. A warning can also be output when the difference between the positions exceeds a boundary value. Alternatively, the force acting on the robot arm can be calculated from the measured position and the rigidity of the robot arm.

A marker device can be understood to mean a single or also a number of markers. The function of a marker is to be detected by a marker detection device (for example, a camera), such that its spatial location (i.e. position and/or orientation) can be ascertained. Such markers can be active markers. An active marker emits for example electromagnetic radiation and/or waves, wherein this radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflection properties. It is also possible for a marker to reflect and/or emit electromagnetic radiation and/or waves in the range of radio frequencies, or at ultrasound wavelengths. A marker preferably has a spherical and/or sphere-like shape and can therefore be referred to as a marker sphere.

A "reference star" designates a device to which a number of marker devices, advantageously three marker devices, are attached, wherein the marker devices are attached stationary and advantageously detachably to the reference star, such that a known location of the marker devices relative to each other is created. In a surgical navigation method, the reference star serves to attach a plurality of marker devices to an object (for example, a bone or a medical instrument), in order to be able to detect the spatial location of the object (i.e. its position and/or orientation). Such a reference star usually includes a way of being attached to the object (for example, a clamp and/or a thread), a holding element which ensures a distance between the marker devices and the object (in particular in order to aid the visibility of the marker devices to a marker detection device) and marker holders which are mechanically connected to the holding element and to which the marker devices can be attached. Where it is clear from the context, the term "reference star" can also refer to a reference star with at least one marker device attached to it. Such a system consisting of a reference star and at least one marker device can also be referred to as a marker star.

Optionally, the rigidity at the current robot arm position is selected by the user as a new boundary rigidity, wherein the working space is recalculated on the basis of this new boundary rigidity.

Optionally, the joint placement is also corrected automatically, wherein the joints are guided such that the positional deviation which is calculated from the rigidity and the forces acting on the robot arm is compensated for.

It is possible to combine different features or applications of the present invention with each other. The positional deviation, which as already described is calculated from the rigidity and the forces acting on the robot arm, can also be respectively used as the criterion instead of the rigidity, wherein the comparison logic has to be adapted. If the rigidity is not for example to fall below a boundary value, then the positional deviation must not exceed a boundary value. Maximizing the rigidity means minimizing the positional deviation, and so on.

The present invention also relates to a software program which is designed to perform the above method. To this end, the software program is for example executed on a computational unit which is connected to a suitable robot arm.

The present invention also relates to a control device for a medical robot arm comprising at least one joint, which is configured to perform the method described above, and to an operation system comprising such a control device and a robot arm.

BRIEF DESCRIPTION OF THE DRAWING

The invention shall be explained in more detail on the basis of an example embodiment.

FIG. 1 shows a medical robot arm comprising seven joints.

DETAILED DESCRIPTION

FIG. 1 shows a robot arm 1 comprising seven joints 3-9. The robot arm 1 is connected to a control unit 2 which guides drives (not shown) for adjusting the joints 3-9 in the robot arm 1. Each drive consists for example of an electric motor which alters the placement of the corresponding joint, wherein a transmission gear is optionally provided. The robot arm 1 also consists of four arm sections 11, 12, 13, 14 and a base part 10. The base part 10 serves to fasten the robot arm 1, i.e. the fastening point of the robot arm 1 is situated on the base part 10. The arm section 14 at the moving end of the robot arm 1 simultaneously forms a holding device 14 for a medical instrument. The spatial position of the holding device 14 can also be referred to as the robot arm position.

The arm section 11 can be rotated via the joint 3 in one axis relative to the support part 10. The arm section 12 can be rotated via the joints 4, 5 in two axes relative to the arm section 11. The arm section 13 can be rotated via the joints 6, 7 about two axes relative to the arm section 12. The accommodating device 14 can be rotated via the joints 8, 9 about two axes relative to the arm section 13. The joints 4, 5, 6, 8 enable a pivoting movement, while the joints 3, 7, 9 enable a torsion movement.

The holding device 14 serves to accommodate a medical instrument such as for example a biopsy needle or a milling head. The robot arm 1 serves to precisely position and move the medical instrument.

Due among other things to the material rigidity of the arm sections 11-14 and the joints 3-9, a deviation occurs between the robot arm position, and therefore the position of the medical instrument, and the theoretical position which follows from the guidance system for the joints 3-9. This is caused on the one hand by the inherent weight of the robot arm 1 and on the other by external forces acting on the robot arm 1. The acting forces are ascertained by force sensors (not shown) which are for example integrated into the joints 3-9.

In order to assess the positional deviations, a rigidity model of the robot arm 1 is stored in the control unit 2. On the basis of the rigidity model and the acting forces, it is possible to calculate the deviation between the actual robot arm position and the theoretical robot arm position according to the joint placement. The result of this calculation and/or the rigidity alone can be used in various ways.

A first option is to predetermine a minimum rigidity and to calculate from this the working space within which the robot arm 1 maintains the required rigidity. When the robot arm 1 is subsequently used, a robot arm position outside of this working space is prevented by the control unit 2. It is in particular possible to check, before the robot arm 1 is used, whether the working space covered with the desired rigidity contains the space necessary for the application. The desired minimum rigidity is for example input by the operator of the robot arm 1 or automatically chosen on the basis of the application scenario.

In accordance with a second option, the anchoring point of the robot arm 1, i.e. the position of the base part 10, is calculated from the rigidity and the working space to be traveled, wherein for example different anchoring points are iteratively assumed and the working space covered by the robot arm 1 with the desired rigidity is calculated for each anchoring point.

The first anchoring point at which the rigidity is maintained for the whole of a working space to be reached is for example chosen. Alternatively, the minimum rigidity for each anchoring point and the working space to be reached is calculated, and the anchoring point with the greatest minimum rigidity is chosen. The minimum rigidity is the rigidity of the robot arm 1 in the position within the working space as a whole for which the rigidity of the arm 1 is at its lowest. In another alternative, the anchoring point with the greatest average rigidity, for which the requirements regarding the minimum rigidity are fulfilled, is chosen. The average rigidity is for example the arithmetical mean of all the rigidities, wherein the rigidities are either weighted equally or are weighted differently for different regions of the working space to be traveled.

In accordance with a third option, a warning is output when the robot arm 1 falls below a defined boundary value for the rigidity. If the operator moves the robot arm 1 to a position at which it falls below the boundary value for the rigidity, then a warning tone for example sounds or a warning signal is displayed.

In accordance with a fourth option, the joint placement for which defined criteria regarding the rigidity are fulfilled is selected from a number of possible joint placements, in order to reach a robot arm position. This is possible if the number of joints is over-determined, i.e. if a robot arm position can be reached using a number of joint placements. In this case, the optimum joint placement is to be determined.

To this end, the number of all possible joint placements is for example determined, and a check is sequentially made for each joint placement as to whether it leads to the desired minimum rigidity. The first joint placement which fulfils the rigidity is then for example selected. Alternatively, the rigidity for each possible joint placement is calculated, and the joint placement which achieves the greatest minimum or average rigidity is selected.

It is possible within the framework of the present invention to combine individual features of the aforesaid options. It is in particular possible, for example, to respectively calculate the rigidity for different joint placements when determining the anchoring point.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, “code” or a “computer program” embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a “means”) are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for assessing the positioning accuracy of a medical robot arm that includes at least one joint and a computational unit operatively coupled to the at least one joint, the computational unit configured to access a rigidity model corresponding to the robot arm, the method comprising:

using the computational unit to calculate and assess a rigidity of the robot arm, said rigidity calculated based on the rigidity model;

calculating a working space which can be traveled by the robot arm based on the calculated rigidity and a predetermined minimum rigidity; and determining if the calculated working space includes a space necessary to perform a specific task.

2. The method according to claim 1, wherein calculating the rigidity of the robot arm includes basing the calculation of the rigidity on mechanical rigidity of the robot arm.

3. The method according to claim 2, wherein calculating the rigidity of the robot arm includes basing the calculation of the rigidity on at least one of a rigidity of the at least one joint or arm sections of the robot arm.

4. The method according to claim 1, wherein calculating the rigidity of the robot arm includes basing the calculation of the rigidity on control rigidity.

5. The method according to claim 1, wherein calculating the working space includes basing the calculation of the working space on a force acting on the robot arm.

6. The method according to claim 1, wherein calculating the working space includes basing the calculation of the working space on a weight of the robot arm.

7. The method according to claim 1, further comprising calculating an anchoring point of the robot arm based on the calculated rigidity and a working space to be traveled by the robotic arm.

8. The method according to claim 1, further comprising outputting a warning when the calculated rigidity of the robot arm falls below a defined boundary value.

9. The method according to claim 1, further comprising selecting from a number of possible joint placements a joint placement of the at least one joint for which predefined criteria regarding the rigidity of the robot arm are fulfilled.

10. The method according to claim 1, further comprising selecting from a number of possible joint placements a joint placement of the at least one joint from which it is possible to reach a predetermined working space using only continuous changes in joint placement without falling below the predetermined minimum rigidity.

11. The method according to claim 1, further comprising comparing a measured robot arm position with a calculated robot arm position, the calculated robot arm position based on the rigidity model.

12. A non-transitory computer readable medium comprising computer executable instructions adapted to perform the method according to claim 1.

13. A control device for a medical robot arm comprising at least one joint, which is configured to perform the method according claim 1.

14. An operation system, comprising a robot arm and a control device according to claim 13.

15. The method according to claim 1, further comprising assessing the positioning accuracy of the robot arm, wherein assessing includes determining a deviation between an actual position of the robot arm and a theoretical position of the robot arm.

16. The method according to claim 15, wherein determining the deviation includes determining the theoretical position of the robot arm based on a position of the at least one joint.

17. A method for controlling a position of a medical robot arm that includes at least one joint and a computational unit operatively coupled to the at least one joint, the computational unit configured to access a rigidity model corresponding to the robot arm, the method comprising:

using the computational unit to calculate a rigidity of the robot arm based on the rigidity model, said calculation performed for a position of the at least one joint that achieves a target position of the robot arm;

comparing the calculated rigidity of the robot arm to a predetermined minimum rigidity value; and the computational unit commanding the at least one joint to the position when the calculated rigidity is greater than the minimum rigidity value.

18. The method according to claim 17, further comprising outputting a warning when the calculated rigidity of the robot arm falls below a defined boundary value.

19. The method according to claim 17, further comprising selecting a joint placement of the at least one joint for which predefined criteria regarding the rigidity of the robot arm are fulfilled.

20. A non-transitory computer readable medium comprising computer executable instructions adapted to perform the method according to claim 17.

21. A control device for a medical robot arm comprising at least one joint, which is configured to perform the method according claim 17.

22. A method for assessing the positioning accuracy of a medical robot arm that includes at least one joint and a computational unit operatively coupled to the at least one joint, comprising:

using the computational unit to calculate a rigidity of the robot arm over a plurality of different positions of the at least one joint based on a rigidity model corresponding to the medical robot arm;

using the calculated rigidity of the medical robot arm to determine positions of the at least one joint that maintain a predetermined minimum rigidity of the medical robot arm.

* * * * *